(12) United States Patent
Middaugh et al.

(10) Patent No.: US 10,046,095 B1
(45) Date of Patent: Aug. 14, 2018

(54) WOUND THERAPY DEVICE AND METHOD

(71) Applicant: Aatru Medical, Inc., Cleveland, OH (US)

(72) Inventors: Richard L. Middaugh, Rocky River, OH (US); Timothy Wojciechowski, Westlake, OH (US); Thomas E. Lash, Chardon, OH (US); Sundar Manickam, Avon Lake, OH (US); John D. Wolter, Berea, OH (US); John Buan, Maple Grove, MN (US)

(73) Assignee: Aatru Medical, LLC, Cleveland, OH (US)

( * ) Notice: Subject to any disclaimer, the term of this patent is extended or adjusted under 35 U.S.C. 154(b) by 0 days.

(21) Appl. No.: 15/478,327

(22) Filed: Apr. 4, 2017

(51) Int. Cl.
*A61M 1/00* (2006.01)
*A61F 13/02* (2006.01)
*C25B 1/00* (2006.01)
*A61F 13/00* (2006.01)

(52) U.S. Cl.
CPC ....... *A61M 1/0088* (2013.01); *A61F 13/0216* (2013.01); *A61M 1/009* (2014.02); *A61M 1/0066* (2013.01); *C25B 1/00* (2013.01); *A61F 2013/00251* (2013.01); *A61M 2205/3337* (2013.01)

(58) Field of Classification Search
CPC .............. A61M 1/0088; A61M 1/0066; A61M 2205/3337; A61M 1/009; A61F 13/0216; A61F 2013/00251; A61F 2013/00246; A61F 2013/00255; A61F 2013/00259; A61F 2013/00263; A61F 2013/00268; F04B 37/02
See application file for complete search history.

(56) References Cited

U.S. PATENT DOCUMENTS 4,875,473 A * 10/1989 Alvarez .............. A61F 13/0243
428/424.6
5,060,642 A * 10/1991 Gilman ................. A61F 13/023
128/888

(Continued)

OTHER PUBLICATIONS

Dictionary.com definition of "solution," www.dictionary.com/browse/solution.*

*Primary Examiner* — Adam Marcetich
*Assistant Examiner* — Jessica Arble
(74) *Attorney, Agent, or Firm* — Rankin, Hill & Clark LLP

(57) ABSTRACT

A wound covering assembly includes a wound covering membrane and a removable layer. The wound covering membrane can allow liquid or air to pass through the wound covering membrane from a wound site covered by the wound covering membrane to ambient and vice versa. The removable layer covers a portion of the wound covering membrane and is removable from the wound covering membrane when the wound covering membrane is affixed to skin around the wound site. The removable layer is configured and connected with the wound covering membrane such that air and liquid are inhibited from passing through the wound covering membrane and the removable layer when the wound covering membrane is affixed to skin surrounding the wound site and the removable layer is connected with the wound covering membrane. The wound covering assembly can be used with a pump assembly to provide negative pressure to the wound site.

25 Claims, 7 Drawing Sheets

(56) References Cited

U.S. PATENT DOCUMENTS

| | | | |
|---|---|---|---|
| 5,533,962 A * | 7/1996 | Peterman | A61F 13/0203 |
| | | | 602/41 |
| 7,507,870 B2 | 3/2009 | Nielsen et al. | |
| 8,425,478 B2 | 4/2013 | Olson | |
| 8,439,894 B1 * | 5/2013 | Miller | A61F 13/00068 |
| | | | 604/313 |
| 8,604,265 B2 | 12/2013 | Locke et al. | |
| 8,764,732 B2 | 7/2014 | Hartwell | |
| 8,795,247 B2 | 8/2014 | Bennett et al. | |
| 8,808,274 B2 | 8/2014 | Hartwell | |
| 9,061,095 B2 | 6/2015 | Adie et al. | |
| 9,168,330 B2 | 10/2015 | Joshi et al. | |
| 9,283,118 B2 | 3/2016 | Locke et al. | |
| 2005/0070835 A1 * | 3/2005 | Joshi | A61M 1/0066 |
| | | | 602/41 |
| 2009/0299251 A1 | 12/2009 | Buan | |
| 2013/0150814 A1 | 6/2013 | Buan | |
| 2015/0057625 A1 * | 2/2015 | Coulthard | A61F 13/00068 |
| | | | 604/319 |
| 2015/0191845 A1 * | 7/2015 | Scherson | C25D 17/10 |
| | | | 417/48 |
| 2015/0320605 A1 | 11/2015 | Pigg | |
| 2016/0361205 A1 | 12/2016 | Mumby | |
| 2017/0028113 A1 * | 2/2017 | Shuler | A61F 13/0216 |

* cited by examiner

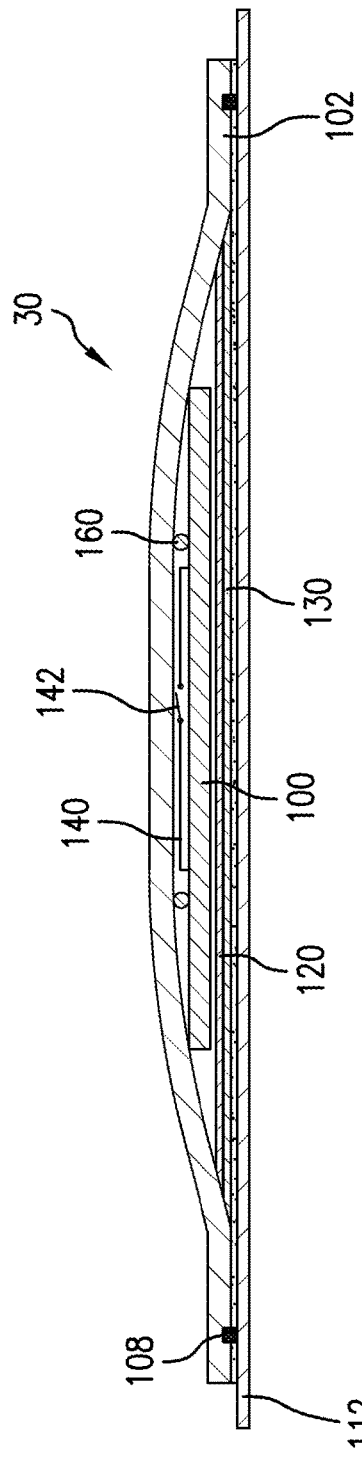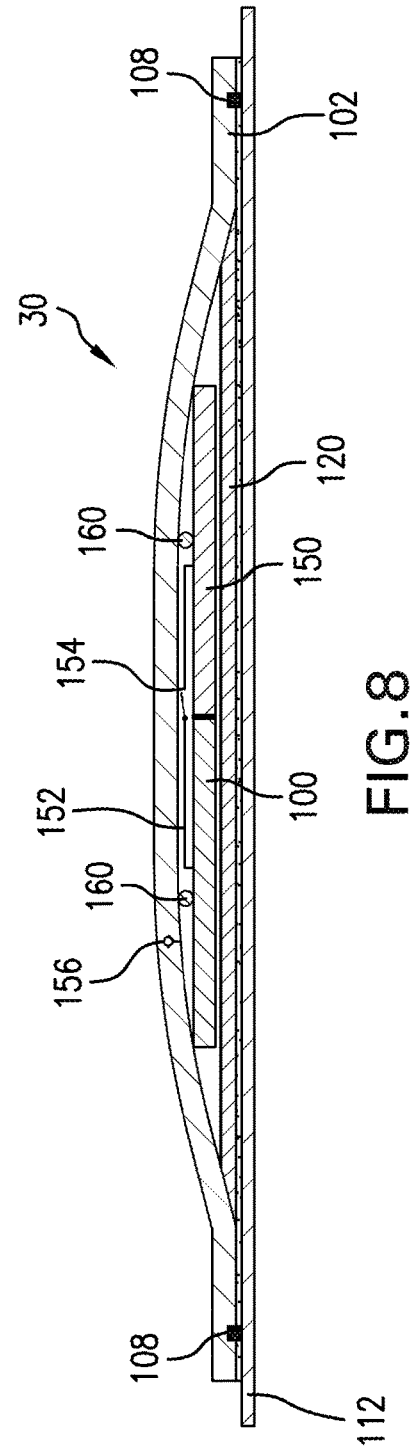

WOUND THERAPY DEVICE AND METHOD

BACKGROUND

Negative pressure is a term used to describe a pressure that is below normal atmospheric pressure. Known topical negative pressure devices range from cumbersome wrinkle reducing suction apparatuses to wound therapies that include fluid-permeable wound cavity filling elements, covering dressings, reasonably air-tight means for sealing against the skin, and drainage tubes connecting the wound site and cavity filling element to the vacuum source via a fluid collection canister.

To enable a more prolonged application of topical negative pressure, powered systems, which include a vacuum generation source such as a pump, have been developed and many examples of such systems are used today for skin treatments and restorative purposes like the temporary removal of wrinkles. Many of these systems, however, are not convenient for users. Such known systems can be large, heavy, noisy, uncomfortable, and not simple for users to apply and initiate a controlled pressure condition. Such known systems also rely on an outside power or vacuum source to create topical negative pressure conditions.

Such tissue treatment, surgery, and other advanced technical interventions are becoming more common given the occurrence of both the aging population, as well as increasingly compromised patient populations. This trend looks set to continue. In wound care, for example, healthcare professionals are now more likely to encounter wounds that are difficult to manage with complex healing problems. Attempts have been made to produce more simple mechanical devices able to apply topical and negative pressure to a tissue site. It will be appreciated that such a medical device, due to its relative simplicity of design, would be expected to reduce material costs and assembly costs. For example, attempts have been made to use a hand-pump system for the application of topical negative pressure at a tissue site. However, such a system fails to enable easier application by the user, discreet use, and prolonged convenient application of topical negative pressure, and, in fact, re-evacuation is often necessary. These can be serious deficiencies, particularly as many such systems are ideally useable for prolonged periods, such as overnight.

SUMMARY

In view of the foregoing, a wound covering assembly includes a wound covering membrane and a removable layer. The wound covering membrane is configured to allow at least one of liquid and air to pass through the wound covering membrane from a wound site covered by the wound covering membrane to ambient and vice versa. The removable layer covers at least a portion of the wound covering membrane. The removable layer is removable from the wound covering membrane when the wound covering membrane is affixed to skin around the wound site. The removable layer is configured and connected with the wound covering membrane such that air and liquid are inhibited from passing through the wound covering membrane and the removable layer when the wound covering membrane is affixed to skin surrounding the wound site and the removable layer is connected with the wound covering membrane.

In combination with the wound covering assembly described above, a pump assembly can also be provided. The pump assembly includes a pump and a pump drape. The pump drape connects with the pump. The pump drape is configured to inhibit passage of air and liquid through the pump drape. The pump drape is also configured to affix to the wound covering membrane or human skin and cover the at least opening after the removable layer has been removed from the wound covering membrane.

In view of the foregoing, a pump assembly for a wound therapy device includes a pump drape, a pump and an air permeable liquid impervious membrane. The pump drape is configured to affix to a wound covering membrane or human skin around a wound site. The pump is covered by the pump drape. The air permeable liquid impervious membrane is connected with at least one of the pump and the pump drape and is located with respect to the pump so as to prevent liquid from contacting the pump when the pump drape is affixed to the wound covering membrane or human skin.

A wound therapy device includes a wound contacting element, a drape, a pump and at least one spacer element. The drape covers the wound contacting element. The pump is covered by the drape. The at least one spacer element is also covered by the drape. The at least one spacer element is configured to maintain spacing between the drape and a wound site covered by the drape when reduced pressure is applied underneath the drape around the wound site.

A method of treating a wound site includes affixing a lower surface of a wound covering membrane, which is configured to allow at least one of liquid and air to pass through the wound covering membrane, to skin surrounding the wound site. The method of treating the wound site further includes removing a removable layer from the wound covering membrane to allow at least one of liquid and air from ambient to pass through the wound covering membrane.

BRIEF DESCRIPTION OF THE DRAWINGS

FIG. 7 is a cross-sectional view of an alternative pump assembly.

FIG. 8 is a cross-sectional view of another alternative pump assembly.

DETAILED DESCRIPTION

Figure 1:
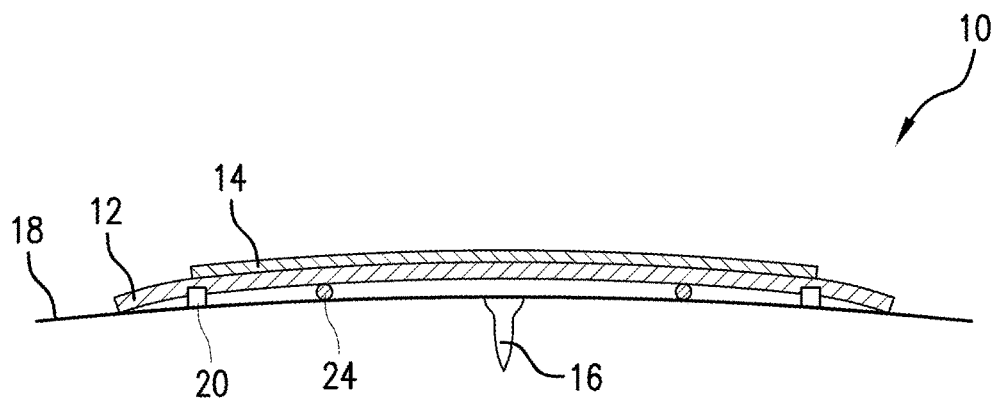
FIG. 1 is a cross-sectional view of a wound covering assembly.

FIG. 1 depicts a wound covering assembly 10 that includes a wound covering membrane 12 and a removable layer 14. The wound covering membrane 12 is configured to allow at least one of liquid and air to pass through the wound covering membrane 12 from a wound site 16 covered by the wound covering membrane 12 to ambient and vice versa. The removable layer 14 covers at least a portion of the wound covering membrane 12. The removable layer 14 is removable from the wound covering membrane 12 when the wound covering membrane 12 is affixed to skin 18 around the wound site 16. The removable layer 14 is configured (e.g., made from a particular material or materials) and connected with the wound covering membrane 12 such that air and liquid are inhibited from passing through the wound covering membrane 12 and the removable layer 14 when the wound covering membrane 12 is affixed to skin 18 surrounding the wound site 16 and the removable layer 14 is connected with the wound covering membrane 12. As such, with the removable layer 14 connected with and covering at least a portion of the wound covering membrane 12, the wound covering assembly 10 is not a "breathable" bandage, and can be referred to as an occlusive bandage.

In the illustrated embodiment, the wound covering membrane 12 is made from a flexible material and can be made from a thin, flexible elastomeric film. Examples of such materials include polyurethane or polyethylene films. Adhesive (not shown) is applied to a skin contacting surface of the wound covering membrane 12 to affix the wound covering membrane 12 to the skin 18. In some instances the wound covering membrane 12 allows only air to pass through, while in other instances the wound covering membrane 12 may allow both air and liquid to pass through. The wound covering membrane 12 may also include openings (not visible in FIG. 1, but another embodiment having at least one opening is described below) and can be configured to inhibit passage of air and liquid through the wound covering membrane 12 other than through the opening(s). For example, the wound covering membrane 12 can made from a material that is air and liquid impermeable, or the wound covering membrane 12 could be coated with a substance, e.g., a hydrogel or a hydrocolloid, or be metallized, to inhibit passage of air and liquid through the wound covering membrane 12 other than through the opening(s). In alternative embodiments, the wound covering membrane 12 can be made from semipermeable materials that can maintain moisture around the wound site 16 while being permeable to water vapor, oxygen, nitrogen and other gases.

Figure 2:
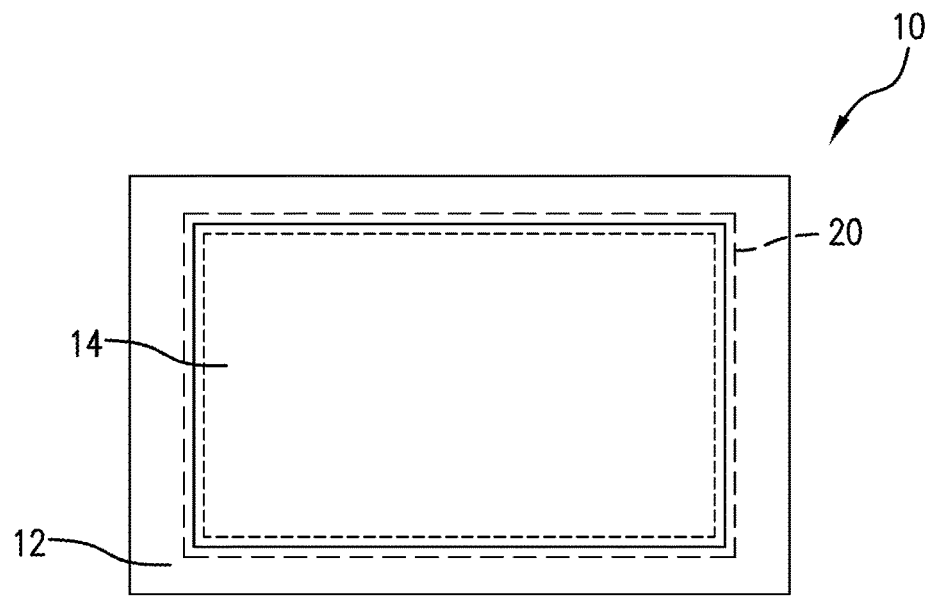
FIG. 2 is a top view of the wound covering assembly depicted in FIG. 1.

The removable layer 14 covers at least a portion of the wound covering membrane 12. Only one removable layer 14 is depicted in FIGS. 1 and 2, however, more than one removable layer 14 can be provided. For example, a plurality of removable layers 14 where each removable layer 14 covers a portion of the wound covering membrane 12. The removable layer 14 can be made from a thin, flexible film. Examples of such materials include polyurethane or polyethylene films. The removable layer 14 is configured to inhibit passage of air and liquid through removable layer 14 when the removable layer 14 is covering and connected with the wound covering membrane 12. The removable layer 14 can made from a material that is air and liquid impermeable, or the removable layer 14 can be coated with a substance, e.g., a hydrogel or a hydrocolloid, or be metallized so as to be air and liquid impermeable.

When the removable layer 14 is removed from the wound covering membrane 12, the wound site 16 is exposed to ambient although through the wound covering membrane 12. When the wound covering membrane 12 is air and liquid pervious, removal of the removable layer 14 can transform the wound covering assembly 10 from an occlusive dressing to a non-occlusive dressing. With the removable layer 14 removed from the wound covering membrane, a pump assembly (examples described below) can be affixed to the wound covering assembly 10 or to the skin 18 to provide negative pressure to the wound site 16, which will be described in more detail below.

The wound covering assembly 10 can also include a sealing element 20 positioned between the skin 18 and the wound covering membrane 12. The sealing element 20 is configured to preclude gas and liquid from passing between the skin 18 and the wound covering membrane 12 when the wound covering membrane 12 is affixed to the skin 18, and is typically in addition to the adhesive used to affix the wound covering membrane 12 to the skin 18. The sealing element 20 operates similar to a gasket and can be made from a hydrogel material, or any other material that can prevent the migration of air and liquid from the wound site 16 under the wound covering membrane 12 and over the skin 18.

With reference to FIG. 2, the removable layer 14 can cover at least the portion of the wound covering membrane 12 bounded by (within) the sealing element 20. When the wound covering membrane 12 is air or liquid permeable, removal of the removable layer 14 can transform the wound covering assembly 10 from an occlusive dressing to a non-occlusive, or "breathable," dressing.

The wound covering assembly 10 can also include at least one spacer element 24 covered by the wound covering membrane 12. The spacer element 24 is configured to maintain spacing between the wound covering membrane 12 and the wound site 16 covered by the wound covering membrane 12 when reduced pressure is applied underneath the wound covering membrane 12 around the wound site 16. The wound covering membrane 12 can be made from a thin film, which allows the wound covering membrane 12 to conform to curves found on the human body but it also tends to be drawn toward the wound site 16 when negative pressure is applied to the wound site 16 underneath the wound covering membrane 12. The spacer element(s) 24 are configured to conform to these curves while maintaining adequate spacing between the wound covering membrane 12 and the wound site 16. Examples of such spacer elements will be described in more detail below with reference to alternative embodiments.

Figure 3:
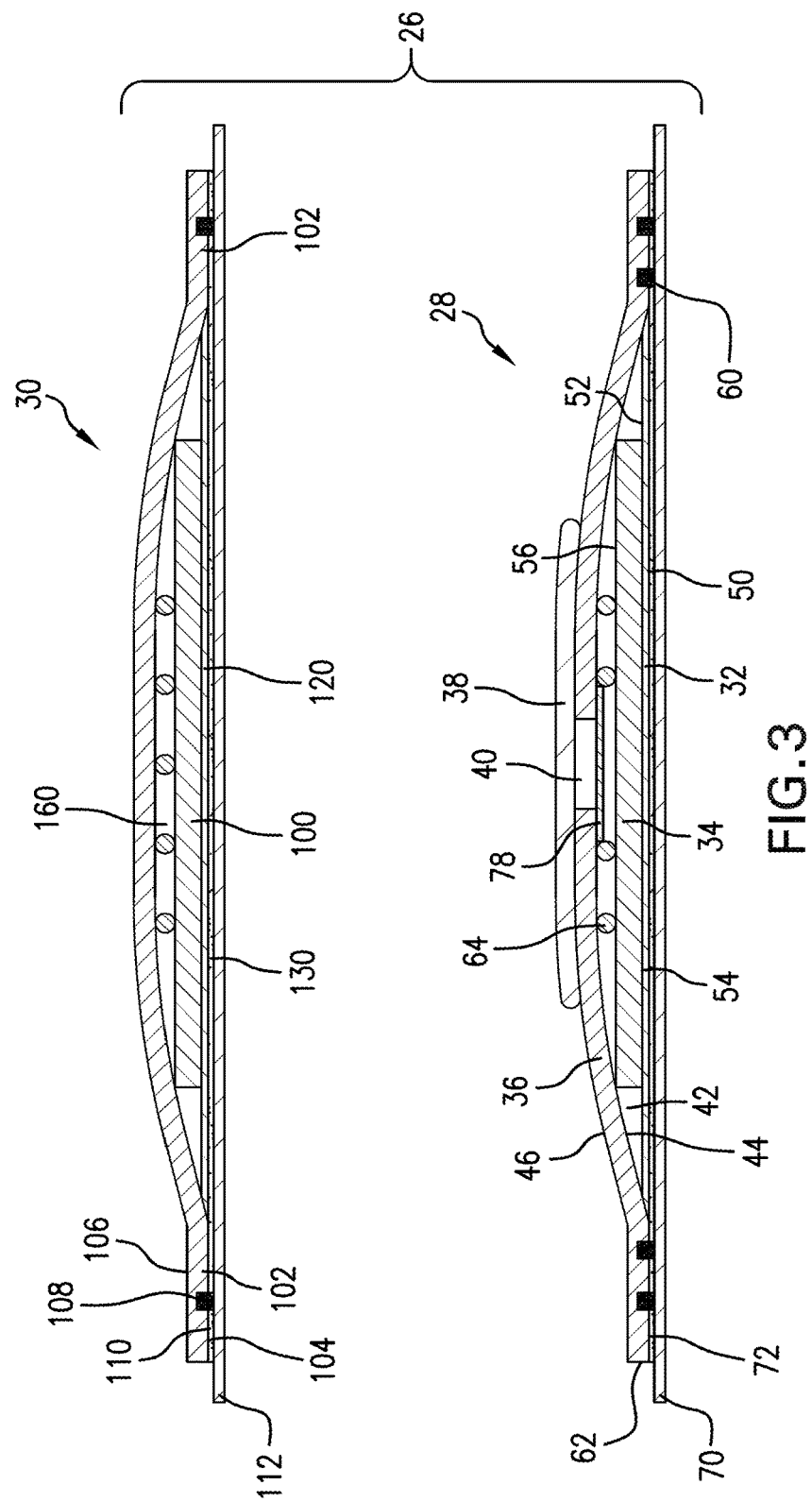
FIG. 3 is a cross-sectional view of a wound therapy device including an alternative wound covering assembly and a pump assembly prior to affixing the pump assembly to the alternative wound covering assembly.
Figure 4:
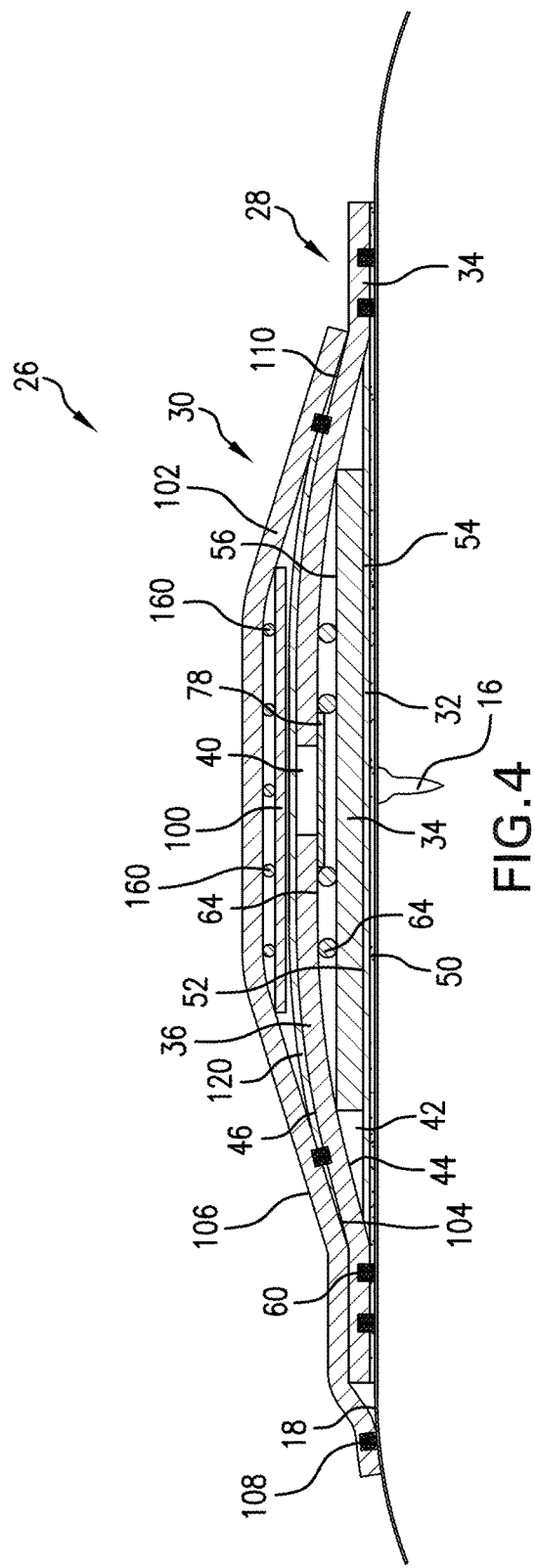
FIG. 4 is a cross-sectional view of the wound therapy device with the pump assembly affixed to the alternative wound covering assembly.

Referring now to FIG. 3, an illustrative embodiment of a wound therapy device 26 includes an alternative wound covering assembly 28 and a pump assembly 30. The wound covering assembly 28 depicted in FIGS. 3 and 4 is similar in function to the wound covering assembly 10 described above. With reference to FIG. 4, the wound covering assembly 28 is affixed to skin 18 surrounding a wound site 16 to cover the wound site 16. The pump assembly 30 can then be affixed to the wound covering assembly 28 or to the skin 18 around the wound site 16 to provide reduced pressure (typically below that of atmospheric pressure) to the wound site 16. The wound covering assembly 28 can also be used to cover the wound site 16 without the use of the pump assembly 30. Depending on the materials chosen to manufacture the wound covering assembly 28, the wound covering assembly 28 can provide an occlusive dressing or a non-occlusive dressing for the wound site.

With reference back to FIG. 3, the wound covering assembly 28 generally includes a wound contacting element, which can include a wound contact layer 32 or a wicking element 34, a wound drape 36, which can be similar in function to the wound covering membrane 12 described above, and a peel away layer 38, which can be similar to the removable layer 14 described above. Accordingly, the wound covering membrane 12 and the wound drape 36 can be used interchangeably, and the removable layer 14 and the peel away layer 38 can also be used interchangeably.

The wound drape 36 covers the wound contacting element, which can be made up of the wound contact layer 32 and the wicking element 34. The wound drape 36 includes at least one opening 40 that extends from a lower (inner) surface 44 of the wound drape 36 to an outer surface 46 of the wound drape 36. The peel away layer 38 covers the opening 40. The peel away layer 38 is releasable from the wound drape 36 when the wound drape 36 is in contact with the skin 18 covering the wound site 16. The peel away layer 38 is connected with the wound drape 36 in a manner such that air and liquid are precluded from passing through the opening 40 in the wound drape 36 from the wound site 16 to ambient, and vice versa, when the wound drape 36 is affixed to the skin 18 surrounding the wound site 16 and the peel away layer 38 is connected with the wound drape 36 covering the opening 40. As such, the wound drape 36 and the peel away layer 38 can define an enclosed volume 42 beneath the wound drape 36 and the peel away layer 38 around the wound site 16 when the wound drape 36 is affixed to the skin 18 surrounding the wound site 16 and the peel away layer 38 is connected with the wound drape 36 covering the opening 40.

The wound contacting element can include the wound contact layer 32 or the wicking element 34. As used herein, the word "or" is not mutually exclusive. The wound contact layer 32 can be made from an elastomeric material, such as a polymeric material that has rubber-like properties. The wound contact layer 32 can be made from an elastomeric material that is a thin, flexible elastomeric film. Examples of such materials include a silver coated nylon, a perforated silicone mesh or other materials that will not stick to human tissue. The wound contact layer 32 can include a plurality of openings (not shown) when used in conjunction with the wicking element 34 to allow exudate from the wound site 16 to pass through the wound contact layer 32 and be retained within the wicking element 34. The wound contact layer 32 includes a skin contacting side 50, which contacts the skin 18 or the wound site 16 when the wound covering assembly 28 is placed over the wound site 16 (see FIG. 2). The wound contact layer 32 also includes an upper side 52 opposite the skin contacting side 50 that faces away from the wound site 16 when the wound covering assembly 28 is affixed to the skin 18 over the wound site 16.

The wicking element 34 can be made from an absorbent material capable of absorbing liquid so as to absorb exudate from the wound site 16. The wicking element 34 includes a skin facing side 54 that faces the skin 18 and the wound site 16 when the wound covering assembly 28 is affixed to the skin 18 over the wound site 16. The wicking element 34 can also include an upper side 56 that is opposite the skin facing side 54 and faces away from the skin 18 when the wound covering assembly 28 is affixed to the skin 18 over the wound site 16. The wicking element 34 can be made from a super absorbent polymers and absorbent beads, foams or natural absorbent materials. The wound covering assembly 28 can also be assembled in a manner, which is described in more detail below, to allow for replacement of the wicking element 34 without removal of the wound contact layer 32.

The wound drape 36 covers the wicking element 34 and the wound contact layer 32. The wound drape 36 can be similar in function to the wound covering membrane 12 described above, and like the wound covering membrane 12 can also be made from a flexible material and can be made from a thin, flexible elastomeric film. Examples of such materials include polyurethane or polyethylene films. The wound drape 36 can be configured to inhibit passage of air and liquid through the wound drape 36 other than through the opening 40. For example, the wound drape 36 can made from a material that is air and liquid impermeable, or the wound drape 36 could be coated with a substance, e.g., a hydrogel or a hydrocolloid, or be metallized, to inhibit passage of air and liquid through the wound drape 36 other than through the opening 40. In alternative embodiments, the wound drape 36 can be made from semipermeable materials that can maintain moisture around the wound site 16 while being permeable to water vapor, oxygen, nitrogen and other gases.

The wound covering assembly 28 further includes a sealing element 60, which operates similarly to the sealing element 20 described above. Since the wound drape 36 can be made from a flexible film-like material, small air passageways may be formed between the skin 18 and the wound drape 36 when the wound drape 36 is affixed to the skin 18 around the wound site 16. The sealing element 60 is positioned on the skin contacting side 50 of the wound contact layer 32 or on the lower surface 44 of the wound drape 36. The sealing element 60 is configured to preclude gas and liquid from passing through any air channels formed between the wound contact layer 32 or the wound drape 36 and the skin 18 and exiting around a peripheral edge 62 of the wound drape 36. The sealing element 60 is configured to preclude gas and liquid from passing between the human skin 18 and the wound contact layer 32 (or the wicking element 34 if the wound contact layer 32 is not included) or the wound drape 36 when the wound drape 36 and the sealing element 60 are applied to the skin 18. The sealing element 60 operates similar to a gasket and can be made from a hydrogel material, or any other material that can prevent the migration of air and liquid from the wound site 16 under the wound drape 36 or the wound contact layer 32 and over the human skin 18. The sealing element 60 is schematically depicted in FIGS. 3 and 4, and can be made to include multiple rings or deposited in a manner to provide a tortuous path through which air and liquid must pass between the human skin 18 and the wound contact layer 32 (or the wicking element 34 if the wound contact layer 32 is not included) or the wound drape 36 when the wound drape 36 and the sealing element 60 are applied to the skin 18.

The wound covering assembly 28 can also include at least one spacer element 64 covered by the wound drape 36 when the wound drape 36 is applied to the human skin 18 around the wound site 16. The spacer element 64 is similar to the spacer element 24 described above. The spacer element 64 is configured to maintain spacing between the wound drape 36 and the wound site 16 covered by the wound drape 36 when reduced pressure is applied in the enclosed volume 42. Since the wound drape 36 can be made from a flexible material, as reduced pressure is applied in the enclosed volume 42, the wound drape 36 may be drawn towards the skin 18 and the wound site 16. In situations where the pump assembly 30 reacts with selected gases in air to remove these selected gases from the enclosed volume 42 to reduce pressure, having the wound drape 36 collapse toward the wound site 16 can result in the pressure in the enclosed volume 42 increasing toward ambient, which is undesirable for negative pressure wound therapy. The spacer element 64 can be a frame structure or similar structural element to provide volume control so as to maintain an appropriate spacing between the wound drape 36 and the wound site 16 when reduced pressure is being applied in the enclosed volume 42. The spacer element 64 could also be a flexible coil spring, which may allow for more flexibility of the wound covering assembly 28 over the wound site 16 when the wound covering assembly 28 is affixed to the skin 18. The spacer element 64 is configured to conform to curves found on the human body while maintaining adequate spacing between the wound drape 36 and the wound site 16.

Other devices could also be used as a spacer element to adequately space the wound drape 36 from the wound site 16 when reduced pressure is being applied in the enclosed volume 42. Also, the wicking element 34 can be configured to provide appropriate voids for gases found in air so that reduced pressure can be maintained. For example, the wicking element 34 can be made from a relatively more rigid foam as compared to the wound drape 36 that maintains gas voids while absorbing exudate from the wound. The wicking element 34 could also be made from the superabsorbent polymers described above that expand and form gas voids, for example between adjacent beads, to provide the aforementioned volume control.

The wound covering assembly 28 can also include a wound drape release liner 70, which can be similar to release liners used in known bandages. The wound drape release liner 70 is disposed over the lower surface 44 of the wound drape 36. The wound drape release liner 70 is removable to expose an adhesive 72 provided on the lower surface 44 of the wound drape 36. The wound drape release liner 70 is removed from the wound drape 36 prior to affixing the wound covering assembly 28 to the skin 18 and over the wound site 16.

Figure 5:
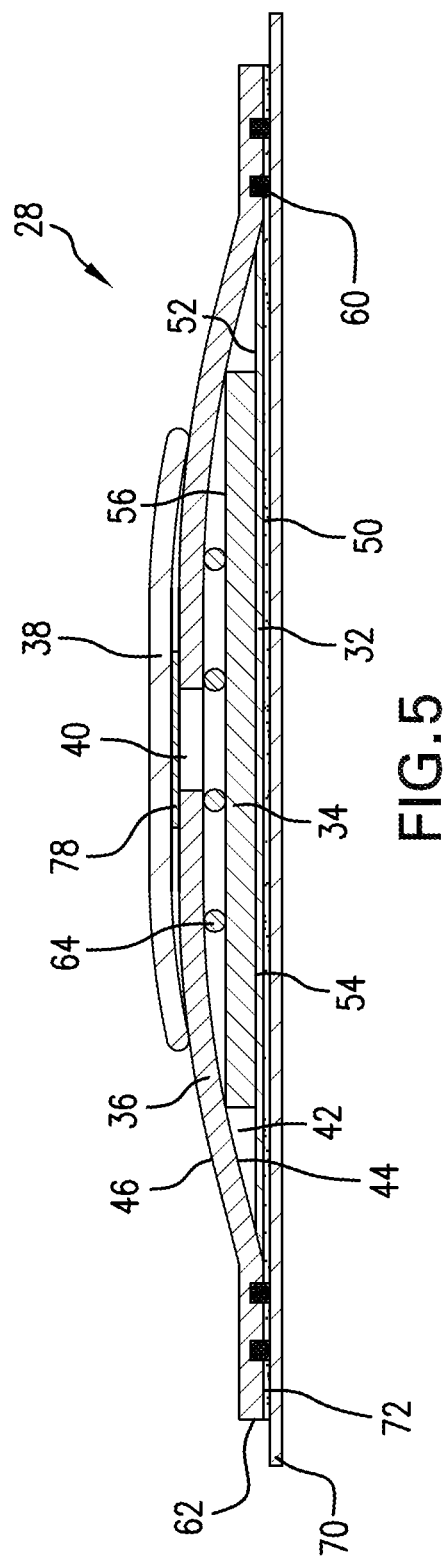
FIG. 5 is a cross-sectional view of another wound covering assembly.

The wound covering assembly 28 can also include an air permeable liquid impervious membrane 78 that covers the opening 40 in the wound drape 36. In the embodiment illustrated in FIGS. 3 and 4, the air permeable liquid impervious membrane 78 is affixed to the lower surface 44 of the wound drape 36; however, the air permeable liquid impervious membrane 78 could also be disposed on the outer surface 46 of the wound drape 36 covering the opening 40 in the wound drape 36, which is shown in FIG. 5. The air permeable liquid impervious membrane 78 precludes liquid (e.g., exudate) from traveling from the wicking element 34 through the opening 40 toward the pump assembly 30 when the pump assembly 30 is affixed to the wound covering assembly 28, such as that shown in FIG. 4. With reference to FIG. 5, when the air permeable liquid impervious membrane 78 is disposed on the outer surface 46 of the wound drape 36, the air permeable liquid impervious membrane 78 can be connected with the wound drape 36 using a resealable adhesive to allow for removal and later reattachment of the air permeable liquid impervious membrane 78 to the wound drape 36, which can allow for the addition or replacement of the wicking element 34. In the embodiment depicted in FIG. 5, the peel away layer 38 is connected with the wound drape 36 in a manner such that removal of the peel away layer 38 does not result in removal of the air permeable liquid impervious membrane 78. For example, in FIG. 5, the peel away layer 38 is larger than the air permeable liquid impervious membrane 78 and connection between the peel away layer 38 and the wound drape 36 (e.g., via adhesive, welding, or the like) is offset from a peripheral edge of the air permeable liquid impervious membrane 78 so that removal of the peel away layer 38 does not necessarily result in removal of the air permeable liquid impervious membrane 78.

Figure 6:
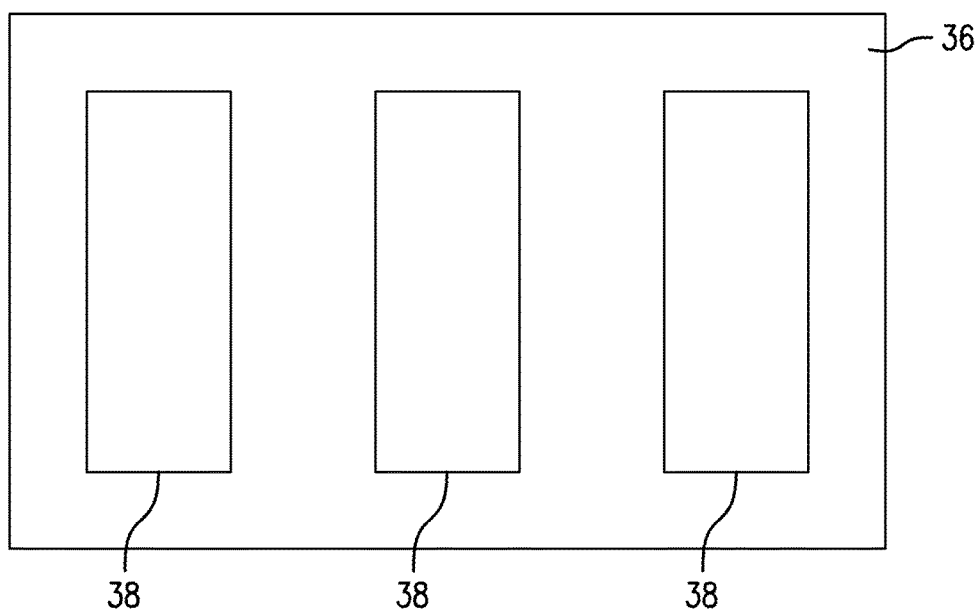
FIG. 6 is a top view of the alternative wound covering assembly.

The peel away layer 38 covers the opening 40 (or openings if more than one is provided) in the wound drape 36. Only one peel away layer 38 is depicted in FIGS. 3-5, however, more than one peel away layer 38 can be provided. For example, FIG. 6 depicts a plurality of peel away layers 38 where each peel away layer 38 covers a respective opening 40 (not visible in FIG. 6) in the wound drape 36. The peel away layer 38 can be made from a thin, flexible film. Examples of such materials include polyurethane or polyethylene films. The peel away layer 38 is configured to inhibit passage of air and liquid through peel away layer 38 when the peel away layer 38 is covering the opening 40 in the wound drape 36. The peel away layer 38 can made from a material that is air and liquid impermeable, or the peel away layer 38 can be coated with a substance, e.g., a hydrogel or a hydrocolloid, or be metallized so as to be air and liquid impermeable.

As mentioned above, the peel away layer 38 is releasable from the wound drape 36 when the wound drape 36 is in contact with the skin 18 and covers the wound site 16. When the peel away layer 38 is removed from the wound drape 36, the opening 40 in the wound drape 36 is exposed to ambient. When the wound drape 36 is air and liquid impervious, removal of the peel away layer 38 can transform the wound covering assembly 28 from an occlusive dressing to a non-occlusive dressing. With the peel away layer 38 removed from the wound drape 36, the pump assembly 30 can be affixed to the wound covering assembly 28 or to the skin 18 to provide negative pressure to the wound site 16. With reference to FIG. 6, one of the peel away layers 38 can be removed and covered by a fitting connected with a mechanical pump (described in more detail below) and a second (or third, for example) peel away layer 38 can be removed exposing the respective opening 40 covered by the second (or third) peel away layer 38 to ambient. This can provide a non-occlusive breathable dressing connected to a mechanical pump, which can be useful with larger wounds that generate a relatively larger amount of exudate.

In the illustrated embodiment, the peel away layer 38 is shown as a separate layer from the wound drape 36 that is connected to the wound drape 36. The peel away layer 38 can be connected to the wound drape 36 via adhesive, welding or another similar connection around a periphery of the peel away layer 38 that would provide an air and liquid impermeable seal at the connection between the peel away layer 38 and the wound drape 36. Alternatively, the peel away layer 38 could be a removable section of the wound drape 36. Score lines can be cut into, but not through, the thickness of the wound drape 36 to define the peel away layer 38.

The pump assembly 30 generally includes a pump 100 and a pump drape 102. The pump drape 102 is configured to affix to the wound drape 36 or the skin 18 around the wound site 16 and cover the opening 40 in the wound drape 36 after the peel away layer 38 has been removed from the wound drape 36. FIG. 2 depicts the left side of the pump drape 102 affixed to the skin 18 and the right side affixed to the wound drape 36. The pump drape 102 could be made larger so that the pump drape 102 contacts the skin 18 and surrounds the peripheral edge 62 of the wound drape 36. Also, the pump drape 102 could be made smaller so that the pump drape 102 is affixed only to the wound drape 36.

The pump drape 102 includes a lower side 104 and an exterior side 106 opposite the lower side 104. The lower side 104 of the pump drape 102 is the side of the pump drape 102 that contacts the outer surface 46 of the wound drape 36 when the pump assembly 30 is affixed to the wound covering assembly 28 or that contacts the skin 18 when the pump drape 102 is affixed to the skin 18. The exterior side 106 of the pump drape 102 is exposed to ambient in the illustrated embodiment.

The pump assembly 30 also includes a pump sealing element, which can include a pump gasket 108 or adhesive 110. The pump sealing element 108, 110 can be positioned on the lower side 104 of the pump drape 102. The adhesive 110 can be an adhesive that is stronger or more aggressive than the adhesive 72 on the wound drape 36, for example when the adhesive 110 only comes in contact with the wound drape 36 and not the skin 18. The pump gasket 108 can be made from the same material, e.g. a hydrogel, and operate similarly to the sealing element 60. The pump gasket 108 can contact the human skin 18, for example when the pump drape 102 is larger than the wound covering assembly 28. The pump sealing element 108, 110 is configured preclude ingress of air between the pump drape 102 and the wound drape 36 when the pump drape 102 is affixed to the wound drape 36 or to preclude ingress of air between the pump drape 102 and the skin 18 when the pump drape 102 is affixed to the skin 18.

The pump assembly 30 also includes a pump drape release liner 112 that covers the pump sealing element, which can be the adhesive 110 or pump gasket 108. The pump drape release liner 112 is removed from the pump drape 102 prior to affixing the pump assembly 30 to the wound covering assembly 28 or the skin 18.

The pump 100 in the pump assembly 30 can be a reactor configured to react with a selected gas found in air, a zinc/air cell, a mechanical pump, or another small pumping device that can provide reduced pressure to the enclosed volume 42 through the opening 40 when the pump assembly 30 is affixed to the wound covering assembly 28. In an embodiment where the pump 100 is a reactor configured to react with a selected gas found in air, the reactor consumes the selected gas in the enclosed volume 42. In the embodiment where the pump 100 is such a reactor, the pump drape 102 covers the pump 100. An example of a reactor that can be used in the pump assembly 30 is described in US 2014/0109890A1. US 2014/0109890A1 describes an oxygen based heater; however, the oxygen based heater can be used as the reactor to consume oxygen within the enclosed volume 42 thus producing a partial vacuum within the enclosed volume 42. The reactor can include a reducing agent, a binding agent on a reactor substrate, and an electrolyte solution, which can be provided in an electrolyte impregnated pad. The reducing agent on the reactor substrate can be zinc, aluminum, or iron, for example.

The pump assembly 30 further includes an air permeable liquid impervious membrane 120, which can be similar to the air permeable liquid impervious membrane 78 that covers the opening 40 in the wound drape 36. In the embodiment where the pump 100 is a reactor that consumes oxygen in the enclosed volume 42, the reactor is interposed between the air permeable liquid impervious membrane 120 and the pump drape 102 when the pump drape 102 is affixed to the wound drape 36 covering the opening 40 in the wound drape 36. The air permeable liquid impervious membrane 120 can also envelope the pump 100.

With reference back to FIG. 3, the pump assembly 30 can also include a removable seal layer 130 that prevents the reactor from being exposed to ambient oxygen until after removal of the removable seal layer 130. In the embodiment where the pump 100 is the reactor configured to react with oxygen, both the pump drape release liner 112 and the removable seal layer 130 are removed from the pump assembly 30 prior to affixing the pump assembly 30 to the wound covering assembly 28 or to the skin 18. If desired, the pump drape release liner 112 can be attached to the removable seal layer 130 so that removal of the pump drape release liner 112 from the pump drape 102 results in removal of the removable seal layer 130 exposing the reactor to ambient. In another alternative arrangement, the pump drape release liner 112 can be affixed to the pump drape 102 in a manner to prevent the pump 100, which in this embodiment would be a reactor configured to consume oxygen, from being exposed to ambient until after removal of only the pump drape release liner 112, e.g., the removable seal layer 130 may not be provided.

As mentioned above, the pump 100 could also be a zinc/air cell. When the pump 100 is a zinc/air cell, the zinc/air cell can react with oxygen found in the enclosed volume 42 (FIG. 3) to remove the oxygen within the enclosed volume 42 thus reducing pressure in the enclosed volume 42. In the embodiment where the pump 100 is a zinc/air cell, which is shown in FIG. 7, the pump drape 102 covers the pump 100. In the embodiment where the pump 100 is a zinc/air cell, a circuit 140 having a normally open switch 142 (both of which are depicted schematically in FIG. 7) can be connected to an anode and cathode, respectively, on the zinc/air cell. An operator can depress the pump drape 102, for example, in the vicinity of the switch 142 to close the switch 142. The zinc/air cell reacts with oxygen in the enclosed volume 42 (FIG. 3) to remove the oxygen from the enclosed volume 42 thus reducing the pressure within the enclosed volume 42. With continued reference to FIG. 7, the pump assembly 30 can also include the air permeable liquid impervious membrane 120 and the removable seal layer 130 that prevents the zinc/air cell from being exposed to ambient oxygen until after removal of the removable seal layer 130.

In lieu of the reactor and zinc/air cell described above, the pump 100 may be one or any combination of electrochemical pumps, vacuum-on-demand devices (referred to herein as VOD), electrolyzers, pressure-reducing solid state devices, oxygen absorbing iron packets, or getters of zirconium titanium, vanadium iron, lithium, lithium metal, magnesium, calcium, lithium barium combinations, zinc-air battery, zinc-air battery components or other materials highly reactive with the selected gases, for example, nitrogen, carbon dioxide and oxygen gases found in wound bed environments.

With reference back to FIG. 3, the pump assembly 30 can further include at least one spacer element 160 covered by the pump drape 102. The spacer element 160 in the pump assembly 30 can be similar in configuration and function to the spacer element 64 provided in the wound covering assembly 28. The spacer element 160 in the pump assembly 30 is configured to maintain spacing between the pump drape 102 and the wound drape 36 when reduced pressure is applied under the wound drape 36, i.e., within the enclosed volume 42.

As discussed above, the pump 100 can also be a mechanical pump. One such embodiment is schematically depicted in FIG. 8. In the embodiment depicted in FIG. 8, the pump assembly 30 can further include a power source 150, which is electrically connected with the pump 100, and is also connected with the pump drape 102. In the embodiment where the pump 100 is a mechanical pump, a circuit 152 can be provided with a normally open switch 154. An operator can depress the pump drape 102, for example, to close the switch 154 to provide power from the power source 150, which can be a small battery, to the pump 100. In the embodiment where the pump 100 is a mechanical pump, a one-way check valve 156 can be provided in the pump drape 102 to allow for gas to move from the enclosed volume 42 through the one-way check valve 156 into ambient; however, ambient air is precluded from passing through the check valve 156 toward the enclosed volume 42.

The pump assembly 30 can also include an opening (similar to the opening 40) in the pump drape 102 covered by a pump peel away layer (similar to the peel away layer 38). Removal of the pump peel away layer can expose the opening in the pump drape 102 to allow for replacement of the pump 100. The pump peel away layer would connect with the pump drape 102 in the same way that the peel away layer 38 connects with the wound drape 36. The pump peel away layer would be made from the same material as the peel away layer 38.

Figure 9:
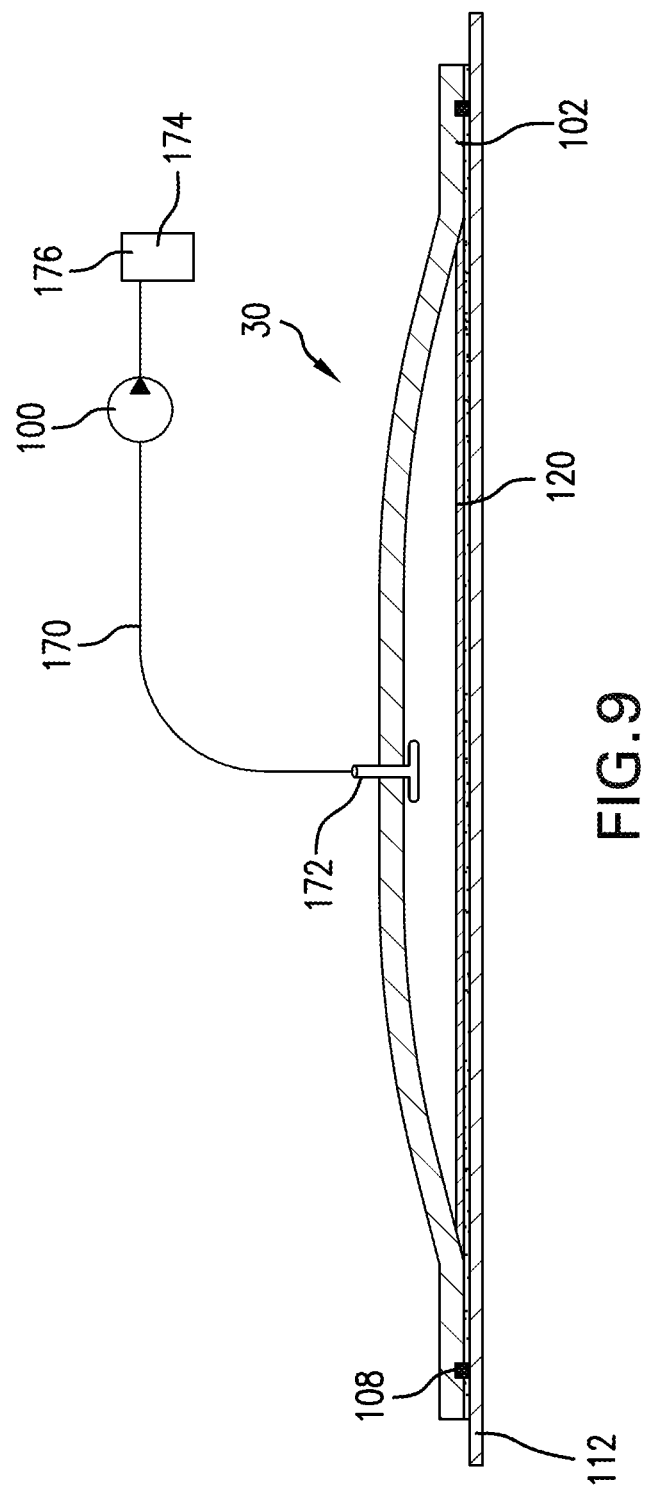
FIG. 9 is a cross-sectional view of another alternative pump assembly.

Another embodiment of a mechanical pump is shown in FIG. 9. In this embodiment, the pump 100 is connected with the pump drape 102 through a fluid line 170 and the pump 100 is located externally from the pump drape 102. A fitting 172 passes through the pump drape 102, and the fluid line 170 connects the fitting 172, which includes an internal passage, with the pump 100. The pump 100 connects with a canister 174 through an exhaust line 176.

A method of treating the wound site 16 will be described with reference to the wound covering assembly 28 depicted in FIG. 3 and the pump assemblies 30 depicted in FIGS. 3, 4 and 7-9. Nevertheless, the method of treating the wound site 16 can be accomplished using a wound covering assembly that is structurally different than the wound covering assembly 28 depicted in FIG. 3 or a pump assembly that is structurally different than the depicted pump assemblies 30.

The method of treating the wound site 16 includes placing the lower surface 44 of the wound drape 36 of the wound covering assembly 28 on the skin 18 surrounding the wound site 16. The method further includes removing the peel away layer 38 from the wound drape 36 to expose the opening 40 to ambient. The method also includes affixing the pump assembly 30 to the wound drape 36 or the skin 18 to cover the opening 40 in the wound drape 36. Where the pump assembly includes a reactor or zinc/air cell configured to react with a selected gas found in air and the removable seal layer 130 that prevents the reactor or zinc/air cell from being exposed to ambient until after removal of the removable seal layer, the method can further include removing the removable seal layer 130 and exposing the pump 100 to ambient prior to affixing the pump assembly 30 to the wound drape 36 or the skin 18. Where the pump assembly includes a zinc/air cell as the pump 100, the method can include closing the electrical circuit 140 (FIG. 7), which includes the zinc/air cell. Also, in the embodiment where the pump assembly includes a mechanical pump as the pump 100, the method can also include closing the electrical circuit 152, which includes the mechanical pump and the power source 150.

Controlling the volume around the wound site 16 can be important to maintain negative pressure. Both the wound drape 36 and the pump drape 102 can be made from thin films that may collapse toward the wound site 16 as gas is being removed from around the wound site. The spacer elements 64, 160 can maintain adequate spacing between the drapes 36, 102 and the wound site 16 or skin 18 when reduced pressure is applied under the drapes 36, 102.

Also, in some instances the peel away layer 38 may not be provided. In instances where the peel away layer 38 is not provided, the wound therapy device 26 can still have a two-piece design, e.g., include the wound covering assembly 28 and the pump assembly 30. In instances where the peel away layer 38 is not provided, the wound drape 36 can include the opening 40 (or multiple openings) that are covered by the pump drape 102 and the remainder of the pump assembly 30. In instances where the peel away layer 38 is not provided, the wound drape 36 can also be made from a material that allows gas to permeate through the wound drape 36.

Alternatively, the wound therapy device 26 can have a one-piece design without the peel away layer 38. In such an instance, the wound contacting element, which can include the wound contact layer 32 or the wicking element 34, a drape (e.g., an outer drape similar to the pump drape 102), the pump 100 and the spacer element (e.g., similar to the spacer element 64, 160) can be provided as one assembly that is affixed to the skin 18 as one unit. In this instance, an inner drape (similar to the wound drape 36 in FIG. 4) may not be provided. In this alternative arrangement, the drape is configured to inhibit passage of air and liquid through the drape. In this alternative arrangement, a sealing element, which is similar to the sealing element 60 described above, can be positioned on a skin contacting side of the wound contacting element or on a lower surface of the drape. In this alternative arrangement, the pump is covered by the drape and can be any of the pumps described above. In this alternative arrangement, the wound therapy device 26 can include an air permeable liquid impervious membrane, similar to the air permeable liquid impervious membrane 120. Where the pump is a reactor, described above, the pump is interposed between the air permeable liquid impervious membrane and the drape when the drape is affixed to skin 18 covering the wound site 16. In this alternative arrangement where the pump is a reactor, the wound therapy device can also include a removable seal layer that prevents the reactor from being exposed to ambient until after removal of the removable seal layer. In this alternative arrangement, the wound therapy device 26 can also include a release liner disposed over a lower surface of the drape, and the release liner is removable to expose an adhesive provided on a lower surface of the drape.

Embodiments of a wound therapy device and methods of treating a wound site have been described above in particularity. Modifications and alterations will occur to those upon reading and understanding the preceding detailed description. The invention, however, is not limited to only the embodiments described above. Instead, the invention is broadly defined by the appended claims and the equivalents thereof. It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A wound covering assembly comprising:
   a wound covering membrane configured to allow at least one of liquid and air to pass through the wound covering membrane from a wound site covered by the wound covering membrane to ambient and vice versa; and
   a removable layer covering at least a portion of the wound covering membrane, the removable layer being removable from the wound covering membrane when the wound covering membrane is affixed to skin around the wound site, the removable layer being configured and connected with the wound covering membrane such that air and liquid are inhibited from passing through the wound covering membrane and the removable layer when the wound covering membrane is affixed to skin surrounding the wound site and the removable layer is connected with the wound covering membrane; and
   a pump assembly including a pump, wherein the pump is a reactor configured to react with a selected gas found in air, wherein the reactor consumes the selected gas;

a pump drape covering the pump and configured to inhibit passage of air and liquid through the pump drape, wherein the pump drape is configured to affix to the wound covering membrane or human skin after the removable layer has been removed from the wound covering membrane.

2. The wound covering assembly of claim 1, further comprising a sealing element positioned between the skin and the wound covering membrane, the sealing element configured to preclude gas and liquid from passing between the skin and the wound covering membrane when the wound covering membrane is affixed to the skin.

3. The wound covering assembly of claim 2, wherein the removable layer covers at least a portion of the wound covering membrane bounded by the sealing element.

4. The wound covering assembly of claim 3, further comprising at least one spacer element covered by the wound covering membrane, wherein the spacer element is configured to maintain spacing between the wound covering membrane and the wound site covered by the wound covering membrane when reduced pressure is applied underneath the wound covering membrane around the wound site.

5. The wound covering assembly of claim 1, wherein the wound covering membrane includes at least one opening and is configured to inhibit passage of air and liquid through the wound covering membrane other than through the at least one opening after the removable layer has been removed.

6. The wound covering assembly of claim 5, further comprising an air permeable liquid impervious membrane covering the at least one opening.

7. The wound covering assembly of claim 6, wherein the air permeable liquid impervious membrane is removably connected with an outer surface of the wound covering membrane and is configured to be resealable to the outer surface of the wound covering membrane after being removed from the wound covering membrane.

8. The wound covering assembly of claim 7, wherein the removable layer is connected with the wound covering membrane in a manner such that removal of the removable layer does not result in removal of the air permeable liquid impervious membrane.

9. The wound covering assembly of claim 1, wherein the wound covering membrane is an air permeable liquid impervious membrane.

10. The wound covering assembly of claim 1, further comprising a wound covering membrane release liner disposed over a lower surface of the wound covering membrane, the wound covering membrane release liner being removable to expose an adhesive provided on the lower surface of the wound covering membrane.

11. The wound covering assembly of claim 1, further comprising a pump sealing element positioned on a lower side of the pump drape, the pump sealing element configured to preclude ingress of air between the pump drape and the wound covering membrane when the pump drape is affixed to the wound covering membrane or to preclude ingress of air between the pump drape and human skin when the pump drape is affixed to human skin.

12. The wound covering assembly of claim 1, wherein the reactor is configured to consume oxygen.

13. The wound covering assembly of claim 1, wherein the reactor is configured to consume nitrogen.

14. The wound covering assembly of claim 1, wherein the reactor includes a reactor substrate, a reducing agent, a binding agent, and an electrolyte solution.

15. The wound covering assembly of claim 1, wherein the pump assembly further includes an air permeable liquid impervious membrane, wherein the reactor is interposed between the air permeable liquid impervious membrane and the pump drape when the pump drape is affixed to the wound covering membrane or human skin after the removable layer has been removed from the wound covering membrane.

16. The wound covering assembly of claim 1, wherein the pump assembly includes a removable seal layer that prevents the reactor from being exposed to ambient until after removal of the removable seal layer.

17. The wound covering assembly of claim 1, wherein the pump includes a zinc/air cell.

18. The wound covering assembly of claim 17, wherein the pump includes a circuit and a switch connected with the zinc/air cell.

19. The wound covering assembly of claim 1, wherein the pump assembly further includes at least one spacer element covered by the pump drape, wherein the spacer element is configured to maintain spacing between the pump drape and the wound covering membrane or human skin when reduced pressure is applied under the wound covering membrane.

20. A method of treating a wound site, the method comprising:
    affixing a lower surface of a wound covering membrane, which is configured to allow at least one of liquid and air to pass through the wound covering membrane, to skin surrounding the wound site;
    removing a removable layer from the wound covering membrane to provide at least one opening in the wound covering membrane which allows at least one of liquid and air from ambient to pass through the at least one opening in the wound covering membrane;
    affixing a pump drape of a pump assembly to the wound covering membrane or human skin to cover the at least one opening in the wound covering membrane, wherein the pump assembly includes a reactor configured to react with a selected gas found in air and the pump drape covers the reactor.

21. The method of claim 20, wherein the pump assembly includes a removable seal layer that prevents the reactor from being exposed to ambient until after removal of the removable seal layer, wherein the reactor consumes the selected gas, and the method further comprising:
    removing the removable seal layer and exposing the reactor to ambient prior to affixing the pump assembly to the wound covering membrane or human skin.

22. A wound covering assembly comprising:
    a wound covering membrane configured to allow at least one of liquid and air to pass through the wound covering membrane from a wound site covered by the wound covering membrane to ambient and vice versa, the wound covering membrane including a removable section being removable from the wound covering membrane when the wound covering membrane is affixed to skin around the wound site, the removable section being configured such that air and liquid are inhibited from passing through the wound covering membrane and the removable section when the wound covering membrane is affixed to skin surrounding the wound site and the removable section has not been removed from the wound covering membrane; and
    a pump assembly including a pump, wherein the pump is a reactor configured to react with a selected gas found in air, wherein the reactor consumes the selected gas;

a pump drape covering the pump and configured to inhibit passage of air and liquid through the pump drape, wherein the pump drape is configured to affix to the wound covering membrane or human skin after the removable layer has been removed from the wound covering membrane.

23. The wound covering assembly of claim 22, wherein the removable section is defined by score lines cut into, but not through, a thickness of the wound covering membrane.

24. The wound covering assembly of claim 22, further comprising a removable seal layer that prevents the reactor from being exposed to ambient until after removal of the removable seal layer.

25. The wound covering assembly of claim 24, further comprising a wound covering membrane release liner disposed over a lower surface of the wound covering membrane, the wound covering membrane release liner being removable to expose an adhesive provided on the lower surface of the wound covering membrane.

\* \* \* \* \*